United States Patent [19]

Murata et al.

[11] Patent Number: 5,648,543
[45] Date of Patent: Jul. 15, 1997

[54] PROCESS FOR PRODUCING 4-NITROSODIPHENYLAMINES OR THEIR SALTS

[75] Inventors: Tetsuo Murata; Hiroyuki Takagi; Yasumi Katayama, all of Niihama, Japan

[73] Assignee: Sumitomo Chemical Company, Limited, Osaka-fu, Japan

[21] Appl. No.: 466,239

[22] Filed: Jun. 6, 1995

Related U.S. Application Data

[63] Continuation of Ser. No. 165,653, Dec. 13, 1993, abandoned.

[30] Foreign Application Priority Data

Dec. 15, 1992 [JP] Japan ................... 4-334437
Apr. 28, 1993 [JP] Japan ................... 5-102628
Apr. 28, 1993 [JP] Japan ................... 5-102629

[51] Int. Cl.$^6$ ................... C07C 207/00
[52] U.S. Cl. ................... 564/410; 564/300; 564/431; 564/433; 564/441
[58] Field of Search ................... 564/410, 431, 564/433, 441, 112, 300

[56] References Cited

U.S. PATENT DOCUMENTS

| | | | |
|---|---|---|---|
| 2,782,235 | 2/1957 | Lantz et al. | 564/410 |
| 4,362,893 | 12/1982 | Kurek | 564/410 |
| 4,518,803 | 5/1985 | Batorewicz et al. | 564/410 |

FOREIGN PATENT DOCUMENTS

| | | | |
|---|---|---|---|
| 0107335 | 5/1984 | European Pat. Off. . | |
| 2935775 | 4/1981 | Germany . | |
| 2-3631 | 1/1990 | Japan . | |
| 0085679 | 6/1958 | Netherlands | 564/112 |
| 772081 | 4/1957 | United Kingdom . | |
| 1539744 | 1/1989 | United Kingdom . | |

OTHER PUBLICATIONS

Patent Abstracts of Japan, Unexamined Applications, C field, 14(126):160 C 699 (Mar. 1990); No. 2-3 631 (Toray Ind. Inc.) and JP-A-2-3 631.
Chemical Abstracts, 81(3):318 (Jul. 1974); Abstract No. 13 356t.

*Primary Examiner*—Shailendra Kumar
*Attorney, Agent, or Firm*—Sughrue, Mion, Zinn, Macpeak & Seas

[57] ABSTRACT

Disclosed is a process for producing a 4-nitrosodiphenylamine of the formula (2)

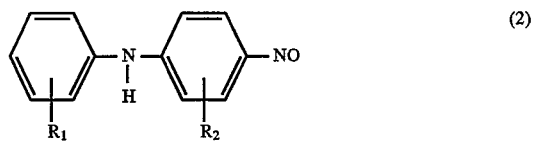

(2)

wherein $R_1$ and $R_2$ independently represent hydrogen atom, methyl group, ethyl group, cyclohexyl group, methoxy group, ethoxy group or chlorine or bromine atom, or a salt thereof, comprising treating a diphenylamine represented by the formula (1)

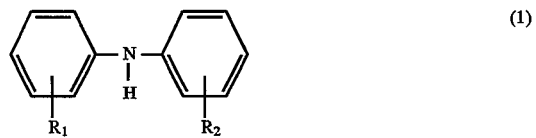

(1)

wherein $R_1$ and $R_2$ are as defined above with (i) a mixture of nitrogen oxides, (ii) a hydrogen halide and (iii) an aliphatic alcohol, wherein the atomic ratio of oxygen to nitrogen of the mixture of nitrogen oxides is more than 1.0 and less than 2.0. This process produces 4-nitrosodiphenylamine of the formula (2) or a salt thereof conveniently and effectively, and is industrially advantageous.

22 Claims, No Drawings

PROCESS FOR PRODUCING 4-NITROSODIPHENYLAMINES OR THEIR SALTS

This is a continuation of application Ser. No. 08/165,653 filed Dec. 13, 1993, now abandoned.

FIELD OF THE INVENTION

The present invention relates to a process for producing 4-nitrosodiphenylamines or their salts, which are useful as intermediates for producing antioxidants for natural rubber and synthetic rubbers and also for producing azo dyes and the like.

BACKGROUND OF THE INVENTION

For producing 4-nitrosodiphenylamines from diphenylamines, the following processes are known: (1) a process comprising adding a solution of hydrogen chloride in an alcohol to a mixture of an aromatic solvent containing a small amount of water, a nitrite salt and a diphenylamine (U.S. Pat. No. 4,362,893); (2) a process comprising reacting diphenylamine with an alkyl nitrite and anhydrous hydrogen chloride in a substantially anhydrous $C_5$–$C_{10}$ aliphatic alcohol solvent free of an aromatic solvent (Japanese Examined Patent Publication (Kokoku) No. Sho 60-42233); (3) a process comprising reacting diphenylamine with nitrosyl chloride and anhydrous hydrogen chloride in a $C_1$–$C_{10}$ aliphatic alcohol solvent (Japanese Unexamined Patent Publication (Kokai) No. Hei 2-3631).

However, in process (1), inorganic salts such as nitrite salt and the like always exist in the state of slurry of poor dispersion due to the use of the nitrite salt in the presence of a small amount of water, so that the reaction between solid and liquid becomes inevitable. Furthermore due to the necessity of controlling the amount of water within a certain range in the solvents, the water content needs be controlled if the solvents are recovered for recycling. In process (2), since the alkyl nitrite to be used as an agent for preparation of nitroso compounds is explosive and decomposable, the storage or preservation thereof is not easy. In process (3), nitrosyl chloride to be used as an agent for preparation of nitroso compounds is an extremely corrosive gas and requires equipment for its generation. Therefore none of the processes reached the satisfactory level for the industrial application.

SUMMARY OF THE INVENTION

An object of the present invention is to provide a convenient and effective process for producing 4-nitrosodiphenylamines or their salts from diphenylamines, which is also good in the industrial application.

This and other objects will become apparent from the following description of the invention.

In the process for producing 4-nitrosodiphenylamines or their salts from diphenylamines, the present inventors have found that a mixture of nitrogen oxides having a specific oxygen/nitrogen atomic ratio can be an excellent agent for preparation of nitroso compounds, and that the process using the nitrogen oxide together with a hydrogen halide and an aliphatic alcohol can satisfy the object described above. Thus, the present invention has been made.

The present invention provides a process for producing a 4-nitrosodiphenylamine represented by the formula (2)

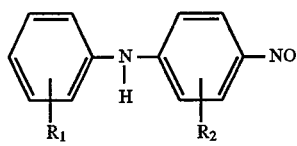

wherein $R_1$ and $R_2$ independently represent hydrogen atom, methyl group, ethyl group, cyclohexyl group, methoxy group, ethoxy group, chlorine atom or bromine atom, or their salts, comprising treating a diphenylamine represented by the formula (1)

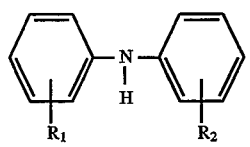

wherein $R_1$ and $R_2$ are as defined above with (i) a mixture of nitrogen oxides, (ii) a hydrogen halide and (iii) an aliphatic alcohol, wherein the atomic ratio of oxygen to nitrogen of the mixture of nitrogen oxides is more than 1.0 and less than 2.0.

DETAILED DESCRIPTION

The details of the present invention will be described below.

Examles of diphenylamines (1) to be used as a starting material in the present invention are diphenylamine, 4-methyldiphenylamine, 4-ethyldiphenylamine, 2-cyclohexyldiphenylamine, 4-cyclohexyldiphenylamine, 2-methoxydiphenylamine, 3-methoxydiphenylamine, 4-methoxydiphenylamine, 4-ethoxydiphenylamine, 4-chlorodiphenylamine, 4-bromodiphenylamine and the like.

The "nitrogen oxides" are usually nitrogen monoxide (NO), nitrogen dioxide ($NO_2$), dinitrogen trioxide ($N_2O_3$) and dinitrogen tetroxide ($N_2O_4$), and the like. Any mixture of nitrogen oxides has its certain equilibrium among the nitrogen oxides.

For example, $NO+NO_2 \rightleftharpoons N_2O_3$

A mixture of nitrogen oxides (hereinafter referred to as "$NO_x$") to be used usually includes at least NO and $NO_2$. $NO_x$ can conveniently be obtained by mixing NO and $NO_2$, and also by mixing NO and $O_2$ as one mole of $NO_2$ is immediately formed by mixing one mole of NO and ½ mole of $O_2$.

The atomic ratio of oxygen to nitrogen (hereinafter referred to as "x") in $NO_x$ to be used should be more than 1.0 but less than 2.0, preferably in the range of 1.1 to 1.8, more preferably in the range of 1.15 to 1.65.

For example, the atomic ratio "x" of $NO_x$ prepared by mixing NO (250 ml/0° C.) and $O_2$ (25 ml/0° C.) is calculated as follows:

$x=(1\times250+2\times25)/(1\times250)=1.20.$ $NO_x$ can be diluted by, for example, an inert gas such as nitrogen gas, argon gas and like rare gas.

$NO_x$ to be used can be caused to act on the diphenylamine of the formula (1), for example, by blowing it.

The amount of $NO_x$ to be used is not particularly limited, but is generally about 0.8 to 10 moles, preferably about 0.9 to 5 moles, more preferably about 1 to 2 moles, per mole of the diphenylamine of the formula (1).

Examples of the hydrogen halide to be used are hydrogen chloride, hydrogen bromide, and the like. Hydrogen chloride is preferred.

Hydrogen halide to be used can be caused to act on the diphenylamine of the formula (1), for example, by blowing it as a gas, or adding it as an aqueous solution.

The amount of the hydrogen halide to be used is usually about 1 to 5 moles, preferably about 1.2 to 3 moles, more preferably about 1.5 to 2.5 moles, per mole of the diphenylamine of the formula (1).

Examples of the aliphatic alcohol to be used are usually those having 1 to 10 carbon atoms. Examples of such aliphatic alcohols are methanol, ethanol, propanol, isopropanol, n-butanol, isobutanol, secondary butanol, tertiary butanol, pentanol, hexanol, heptanol, octanol, 2-ethylhexanol, nonanol, decanol, and the like. Aliphatic alcohols with 4 to 8 carbon atoms such as, for example, n-butanol, isobutanol, secondary butanol, tertiary butanol, pentanol, hexanol, heptanol, octanol, 2-ethylhexanol are preferred. A mixture of at least two kinds of these aliphatic alcohols can also be used. The aliphatic alchohol can be used also as a solvent.

The amount of the aliphatic alcohol is usually at least about ¼ part (0.25 part) by weight, preferably about 1 to 5 parts by weight, per part by weight of the diphenylamine of the formula (1). In the case that such aliphatic alcohol is used as a solvent as well, its amount is usually about 2 to 20 parts by weight, preferably about 3 to 10 parts by weight, per part by weight of the diphenylamine of the formula (1).

Solvent is usually used in the present invention. As the solvent, the above-mentioned aliphatic alcohol, non-reactive solvent such as toluene and chloroform, water, and the like can be used singly or at least two of them can be used in admixture. Preferably, the aliphatic alcohol is used singly or in combination with other solvent.

The amount of the solvent is usually about 2 to 20 parts by weight, preferably about 3 to 10 parts by weight, per part by weight of the diphenylamine of the formula (1).

The process in the present invention is usually conducted at atmospheric pressure or at elevated pressure. Usually, the reaction at atmospheric pressure is enough.

The process according to the present invention can be carried out in various ways. For example, a solution of the diphenylamine of the formula (1) and an aliphatic alcohol in a solvent is treated with a hydrogen halide and $NO_x$ in this or reverse order or at the same time; or the diphenylamine of the formula (1) is first made into a salt by reaction with a hydrogen halide and then the resulting hydrogen halide salt is treated with an aliphatic alcohol and $NO_x$. Preferably, a solution of the diphenylamine of the formula (1) and an aliphatic alcohol in a solvent is treated with a hydrogen halide of the formula (1) with $NO_x$ or hydrogen halide. The and $NO_x$ in this order or at the same time. If necessary, aging can be conducted after contacting the diphenylamine process can be carried out on a batchwise or continuous basis.

The process of the invention can be conducted at a temperature from about 0° to 60° C. preferably from about 20° to 40° C.

Though the reaction time depends on the the amount of hydrogen halide, aliphatic alcohol and $NO_x$ the diphenylamine of the formula (1) with $NO_x$ is usually used, the way how the reaction is conducted and other factors, it is preferable that the time for contacting about 0.5 to 5 hours, and that the aging time is usually about 0.5 to 10 hours.

After the reaction, isolation of the desired product, i.e., 4-nitrosodiphenylamine of the formula (2) or a salt thereof can be conducted in various ways in the present invention. For example, after neutralizing the reaction mixture by an aqueous alkali solution in accordance with a conventional way, the desired product can be obtained by crystallization, and if necessary, by filtration. In the case that hydrogen halide salt of 4-nitrosodiphenylamine of the formula (2) is precipitated in the reaction mixture, the salt can be obtained as it is and, if necessary, by filtration.

Usually, the hydrogen halide salt of 4-nitrosodiphenylamine of the formula (2) is present in the reaction mixture as suspended in the solvent, i.e., in the form of a slurry. When an excess aqueous alkali solution is added to the reaction mixture, unreacted hydrogen halide remaining in the reaction mixture is first neutralized, and subsequently the hydrogen halide salt is neutralized. The released free 4-nitrosodiphenylamine of the formula (2) is neutralized with an alkali to form an alkali metal salt of the 4-nitrosodiphenylamine of the formula (2), which dissolves in the aqueous phase.

Thus, the desired product can be obtained as an aqueous solution of an alkali metal salt of 4-nitrosodiphenylamine of the formula (2) by contacting the reaction mixture with an aqueous alkali solution such as aqueous solution of an alkali metal hydroxide, alkali metal carbonate, alkali metal hydrogencarbonate, and the like.

When the desired product is obtained in the form of an aqueous solution of an alkali metal salt of 4-nitrosodiphenylamine of the formula (2), preferred examples of alkali compound contained in said aqueous alkali solution to be used are sodium hydroxide or potassium hydroxide, sodium carbonate or potassium carbonate, sodium hydrogencarbonate or potassium hydrogencarbonate. Sodium hydroxide and potassium hydroxide are more preferred for industrial use. The amount of the aqueous solution of the alkali compound is usually about 2 to 5 gram equivalents, preferably about 3 to 4 gram equivalents, per mole of the diphenylamine of the formula (1), calcualted as the alkali compound. There is no particular restriction on the concentration of the alkali comound in the aqueous alkali solution, but it is generally preferable to adjust the concentration of the alkali comound to about 1 to 25% by weight.

The aqueous soltuion of an alkali metal salt of the 4-nitrosodiphenylamine of the formula (2) can be obtained effectively, for example, by adding the reaction mixture to said aqueous alkali solution or by adding said aqueous alkali solution to the reaction mixture. When the operation is carried out on a continuous basis, it is preferable to mix the reaction mixture and the aqueous alkali solution simultaneously by feeding into a reactor said aqueous alkali solution from one conduit and the reaction mixture from another conduit. The temperature at which the mixing of the reaction mixture and the aqueous alkali solution is effected is not particularly limited. The reaction is exothermic, and it is usually desirable to conduct the mixing at about −20° to 50° C., preferably at about 0° to 30° C. in the case of adding the reaction mixture to the aqueous alkali solution, and at about −20° to 10° C., preferably about. 0° to 10° C. in the case of adding the aqueous alkali solution to the reaction mixture, optionally by the use of a conventional cooling device. When the mixing operation is carried out on a continuous basis as mentioned above, it is preferable that the feeding rate of the reaction mixture and the feeding rate of the aqueous alkali solution are adjusted to such rates that the temperature of the reaction system is maintained from about −20° to 50° C. preferably from about 0° to 30° C.

When hydrophobic solvent, such as toluene or chloroform, is used in the treatment of the diphenylamine of the formula (1) with $NO_x$, a hydrogen halide and an aliphatic alcohol, the desired aqueous solution of an alkali metal salt of the 4-nitrosodiphenylamine represented by the formula (2) can be separated from the solvent by a conventional separation technique.

Examples of the salt of the 4-nitrosodiphenylamines of the formula (2) prepared by the process of the invention are typically hydrochloride, hydrobromide, an alkali metal salt and the like.

By the process in accordance with the present invention, 4-nitrosodiphenylamines of the formula (2) or their salts can be produced conveniently and effectively from diphenylamines of the formula (1). In addition, the process is advantageous in the industrial application. The resulting 4-nitrosodiphenylamines of the formula (2) or their salts are useful as an intermediate for producing antioxidants for natural rubber and synthetic rubbers, such as N'-alkyl-N-phenyl-p-phenyldiamines, and also useful as an intermediate for producing azo dyes and the like.

EXAMPLE

The following examples illustrate the present invention in more detail. However, the present invention is not limited to such examples.

Example 1

A 33.8 g (0.2 mole) quantity of diphenylamine was added to a mixture composed of 100 ml of toluene and 100 ml of 2-ethylhexanol. Then, 14.6 g (0.4 mole) of hydrogen chloride gas was blown into the mixture through a gas inlet under stirring for about 30 minutes, while maintaining the mixture at 30° C. Then, $NO_x$ (x=1.2, 22.2 g/hour) prepared beforehand by mixing nitrogen monoxide (250 cc/min. at 0° C.) and oxygen (25 cc/min. at 0° C.) was blown into the mixture through a gas inlet at 30° C. for 60 minutes. After blowing, the reaction was continued at 30° C. for 2 hours.

To the resulting mixture in the form of a slurry was added 206 g of a 14 wt. % aqueous sodium hydroxide solution to form a basic mixture, and the resulting mixture was vigorously stirred to fully effect distribution of the resulting 4-nitrosodiphenylamine into the aqueous phase. The amount of the 4-nitrosodiphenylamine in the aqueous phase was 37.6 g (yield 95%). In the oil phase, 0.8 g of N-nitrosodiphenylamine remained. The N-nitrosodiphenylamine can be recovered for potential use as a raw material of 4-nitrosodiphenylamine.

Example 2

A 33.8 g (0.2 mole) quantity of diphenylamine was added to a mixture composed of 100 ml of toluene and 100 ml of 2-ethylhexanol. Then, 14.6 g of hydrogen chloride gas was blown into the mixture through a gas inlet under stirring for about 30 minutes, while maintaining the mixture at 30° C. Then, $NO_x$ (x=1.5, 10.2 g/hour) prepared beforehand by mixing nitrogen monoxide (100 cc/min. at 0° C.) and oxygen (25 cc/min. at 0° C.) was blown into the mixture through a gas inlet at 30° C. for 60 minutes. After blowing, the reaction was continued at 30° C. for 2 hours.

To the resulting mixture was added a 206 g of 14 wt. % aqueous sodium hydroxide solution to form a basic mixture, and the resulting mixture was vigorously stirred to fully effect distribution of the resulting 4-nitrosodiphenylamine into the aqueous phase. The amount of the 4-nitrosodiphenylamine in the aqueous phase was 37.2 g (yield 94%). In the oil phase, 0.8 g of N-nitrosodiphenylamine remained.

Example 3

A 33.8 g quantity of diphenylamine was added to a mixture composed of 100 ml of toluene and 100 ml of 2-ethylhexanol. Then, 40.6 g of 36 wt. % hydrochloric acid was added dropwise to the mixture, while maintaining the mixture at 30° C. Then, $NO_x$ (x=1.5, 10.2 g/hour) prepared beforehand by mixing nitrogen monoxide (100 cc/min. at 0° C.) and oxygen (25 cc/min. at 0° C.) was blown into the mixture through a gas inlet at 20° C. for 60 minutes. After blowing, the reaction was continued at 30° C. for 4 hours. And then, extraction of 4-nitrosodiphenylamine into an aqueous phase was carried out as in Example 1. The amount of 4-nitrosodiphenylamine in the aqueous phase was 30.9 g (yield 78%). In the oil phase, 5.1 g of N-nitrosodiphenylamine remained.

Example 4

In a 1-liter reactor for continuous reaction, 699 g of a 14.5 wt % solution of diphenylamine in a mixture of toluene and 2-ethylhexanol (the weight ratio of toluene and 2-ethylhexanol is 1/1) was maintained at 30° C. under stirring, and the reaction was conducted for 3 hours by blowing into the solution hydrogen chloride at a rate of 14.6 g/hour and $NO_x$ (x=1.5; a mixture of nitrogen monoxide and oxygen at volume ratio of 4:1) at a rate of 9.1 g/hour.

After the reaction, continuous reaction for preparing 4-nitrosodiphenylamine was started. Namely, a 14.5 wt % solution of diphenylamine in a mixture of toluene and 2-ethylhexanol (the weight ratio of toluene and 2-ethylhexanol is 1/1) was fed to the reactor at a rate of 233 g/hour, while each of the hydrogen chloride and $NO_x$ blowing was maintained at the same rate as described above. The reaction solution discharged from the reactor was introduced into an aging reactor, where the solution was maintained at 30° C. for 3 hours of retention time.

The following Table 1 shows the concentrations of 4-nitrosodiphenylamine (abbreviated as "PNDA"), N-nitrosodiphenylamine (abbreviated as "NNDA") and diphenylamine (abbreviated as "DPA"), which were discharged from the aging reactor during the continuous reaction. As the result of the continuous 18 hours reaction, the yields of PNDA, NNDA and DPA calculated from the average values of the concentrations thereof were 96.2%, 1.78% and 0.85%, respectively.

TABLE 1

| reaction time (hr.) | PNDA (wt %) | NNDA (wt %) | DPA (wt %) |
| --- | --- | --- | --- |
| 4 | 14.4 | 0.27 | 0.12 |
| 6 | 12.8 | 0.24 | 0.11 |
| 8 | 14.8 | 0.29 | 0.11 |
| 12 | 14.8 | 0.31 | 0.18 |
| 14 | 15.0 | 0.36 | 0.17 |
| 16 | 14.9 | 0.19 | 0.06 |
| 18 | 15.1 | 0.21 | 0.05 |
| AVERAGE VALUE | 14.6 | 0.27 | 0.11 |

Example 5

A 67.6 g (0.4 mole) quantity of diphenylamine was added to a mixture composed of 170 ml of toluene and 170 ml of 2-ethylhexanol. Then, 29.2 g of hydrogen chloride gas was blown into the mixture through a gas inlet under stirring for about 2 hours, while maintaining the mixture at 30° C. Then, $NO_x$ (x=1.43, 10.3 g/hour) prepared beforehand by mixing nitrogen monoxide (104.5 cc/min. at 0° C.) and oxygen (21.8 cc/min. at 0° C.) was blown into the mixture through a gas inlet at 30° C. for 2 hours. After blowing, the reaction was continued at 30° C. for 2 hours. The resulting mixture was added dropwise to 411 g of a 14 wt. % aqueous sodium hydroxide solution for 2 hours at about 5° C.

The amount of the resulting 4-nitrosodiphenylamine in the aqueous phase was 71.2 g (yield 90%; selectivity 95%). In the oil phase, 3.8 g (recovery, 5%) of diphenylamine remained. The diphenylamine can be recovered for potential use as a raw material of the 4-nitrosodiphenylamine.

Comparative Example 1

A 33.8 g (0.2 mole) quantity of diphenylamine was added to a mixture composed of 85 ml of toluene and 85 ml of 2-ethylhexanol. Then, 14.6 g of hydrogen chloride gas was blown into the mixture through a gas inlet under stirring for about 1 hour, while maintaining the mixture at 30° C. Then, nitrogen monoxide (74.7 cc/min. at 0° C., 6.0 g/hour) was blown through a gas inlet into the mixture at 30° C. for 1 hour. After blowing, the reaction was continued at 30° C. for 2 hours.

The resulting mixture was added dropwise to 206 g of a 14 wt. % aqueous sodium hydroxide solution for 1 hour at about 5° C. The amount of the resulting 4-nitrosodiphenylamine in the aqueous phase was 1.4 g (yield 3.5%; selectivity 66%). In the oil phase, 32 g (recovery 95%) of diphenylamine remained.

Comparative Example 2

A 33.8 g quantity of diphenylamine was added to a mixture composed of 85 ml of toluene and 85 ml of 2-ethylhexanol. Then, 14.6 g of hydrogen chloride gas was blown into the mixture through a gas inlet under stirring over about 1 hour, while maintaining the mixture at 30° C. Then, $NO_x$ (x=2.0, 9.2 g/hour) prepared beforehand by mixing nitrogen monoxide (74.7 cc/min. at 0° C.) and oxygen (37.3 cc/min. at 0° C.) was blown into the mixture through a gas inlet at 30° C. for 1 hour. After blowing, the reaction was continued at 30° C. for 1 hour.

The resulting mixture was added dropwise to 206 g of a 14 wt. % aqueous sodium hydroxide solution for 1 hour at about 5° C. The amount of the resulting 4-nitrosodiphenylamine in the aqueous phase was 16.8 g (yield 42%; selectivity 69%). In the oil phase, 13.1 g (recovery 39%) of diphenylamine remained.

What is claimed is:

1. A process for producing a 4-nitrosodiphenylamine represented by the formula (2)

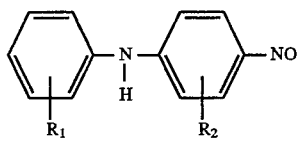

(2)

wherein $R_1$ and $R_2$ independently represent a hydrogen atom, methyl group, ethyl group, cyclohexyl group, methoxy group, ethoxy group, chlorine atom or bromine atom, or a salt thereof, comprising treating a solution of a diphenylamine represented by the formula (1)

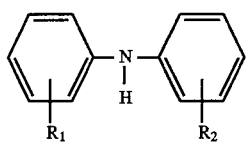

(1)

wherein $R_1$ and $R_2$ are as defined above and an aliphatic alcohol in a solvent with (i) a hydrogen halide and (ii) a mixture of nitrogen oxides in this order or at the same time at a temperature from about 0° to 60° C., wherein the atomic ratio of oxygen to nitrogen of the mixture of nitrogen oxides is more than 1.0 and less than 2.0.

2. A process according to claim 1, wherein the mixture of nitrogen oxides includes at least nitrogen monoxide and nitrogen dioxide.

3. A process according to claim 1, wherein the atomic ratio of oxygen to nitrogen in the mixture of nitrogen oxides ranges from 1.1 to 1.8.

4. A process according to claim 1, wherein the atomic ratio of oxygen to nitrogen in the mixture of nitrogen oxides ranges from about 1.15 to 1.65.

5. A process according to claim 1, wherein the hydrogen halide is hydrogen chloride or hydrogen bromide.

6. A process according to claim 5, wherein the hydrogen halide is hydrogen chloride gas or an aqueous solution of hydrogen chloride.

7. A process according to claim 4, wherein the hydrogen halide is hydrogen chloride gas or an aqueous solution of hydrogen chloride.

8. A process according to claim 1, wherein the hydrogen halide is used in an amount of about 1.2 to 3.0 moles per mole of the diphenylamine of the formula (1).

9. A process according to claim 1, wherein the aliphatic alcohol is a $C_1$–$C_{10}$ aliphatic alcohol.

10. A process according to claim 9, wherein the aliphatic alcohol is a $C_4$–$C_8$ aliphatic alcohol.

11. A process according to claim 1, wherein the treating is carried out by bringing the solution of the diphenylamine of the formula (1) and the aliphatic alcohol in a solvent into contact with the hydrogen halide and the mixture of nitrogen oxides at the same time.

12. A process according to claim 4, wherein the treating is carried out by treating the solution of the diphenylamine of the formula (1) and the aliphatic alcohol in a solvent with the hydrogen halide and the mixture of nitrogen oxides at the same time.

13. A process for producing an alkali metal salt of 4-nitrosodiphenylamine represented by the formula (2)

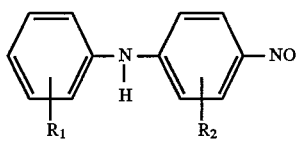

(2)

wherein $R_1$ and $R_2$ independently represent a hydrogen atom, methyl group, ethyl group, cyclohexyl group, methoxy group, ethoxy group, chlorine atom or bromine atom, or a salt thereof, comprising the steps of 1) treating a solution of a diphenylamine represented by the formula (1)

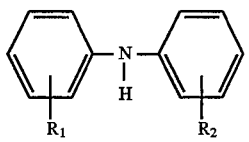

(1)

wherein $R_1$ and $R_2$ are as defined above and an aliphatic alcohol in a solvent with (i) a hydrogen halide and (ii) a mixture of nitrogen oxides in this order or at the same time at a temperature from about 0° to 60° C., wherein the atomic ratio of oxygen to nitrogen of the mixture of nitrogen oxides is more than 1.0 and less than 2.0; and 2) contacting the reaction mixture obtained in step 1) with an aqueous alkali solution.

14. A process according to claim 13, wherein the reaction mixture obtained in step 1) is contacted with the aqueous alkali solution by adding the reaction mixture to the aqueous alkali solution.

15. A process according to claim 13, wherein the reaction mixture obtained in step 1) is contacted with the aqueous alkali solution on a continuous basis by feeding into a reactor the reaction mixture obtained in step 1) from one conduit and the aqueous alkali solution from a different conduit and mixing them simultaneously.

16. A process according to claim 13, wherein the aqueous alkali solution is selected from the group consisting of aqueous solutions of an alkali metal hydroxide, alkali metal carbonate and alkali metal hydrogencarbonate.

17. A process according to claim 14, wherein the aqueous alkali solution is selected from the group consisting of aqueous solutions of sodium hydroxide, potassium hydroxide, sodium carbonate, potassium carbonate, sodium hydrogencarbonate and potassium hydrogencarbonate.

18. A process according to claim 17, wherein the aqueous alkali solution is an aqueous solution of sodium hydroxide or potassium hydroxide.

19. A process according to claim 1, wherein the solvent is an aliphatic alcohol, a non-reactive solvent or water.

20. A process according to claim 1, wherein the solvent is a non-reactive solvent.

21. A process according to claim 13, wherein the solvent is an aliphatic alcohol, a non-reactive solvent or water.

22. A process according to claim 13, wherein the solvent is a non-reactive solvent.

* * * * *